United States Patent [19]

Takase

[11] Patent Number: 5,052,408
[45] Date of Patent: Oct. 1, 1991

[54] APPARATUS USING MICROWAVES FOR THERMOTHERAPY

[76] Inventor: Haruo Takase, 20-16, 3-chome, Shimoochiai, Shinjuku-ku, Tokyo, Japan

[21] Appl. No.: 371,129
[22] Filed: Jun. 26, 1989

[30] Foreign Application Priority Data

Nov. 24, 1988 [JP] Japan .............. 63-152986[U]

[51] Int. Cl.$^5$ .............................................. A61N 5/02
[52] U.S. Cl. .............................. 128/804; 219/10.55 F
[58] Field of Search ..................... 128/804, 399; 219/10.55 R, 10.55 F; 269/322; 600/22

[56] References Cited

U.S. PATENT DOCUMENTS 3,326,203 6/1967 Goertzel ........................... 600/22
4,230,129 10/1980 LeVeen ........................... 128/804
4,316,474 2/1982 Spethmann ...................... 128/804
4,434,341 2/1984 Busby ............................ 128/804 X

FOREIGN PATENT DOCUMENTS 2701934 7/1978 Fed. Rep. of Germany ...... 128/804

Primary Examiner—Lee S. Cohen
Attorney, Agent, or Firm—Oblon, Spivak, McClelland, Maier & Neustadt

[57] ABSTRACT

In a medical apparatus using microwaves, a treating bed for carrying a patient to be subjected to thermal treatment is mounted slidably in and out of a microwave irradiation region defined within a protective frame so as to allow the patient to get on and off without difficulty. The slidable bed while carrying the patient can readily be placed in and out of the microwave irradiation region.

8 Claims, 3 Drawing Sheets

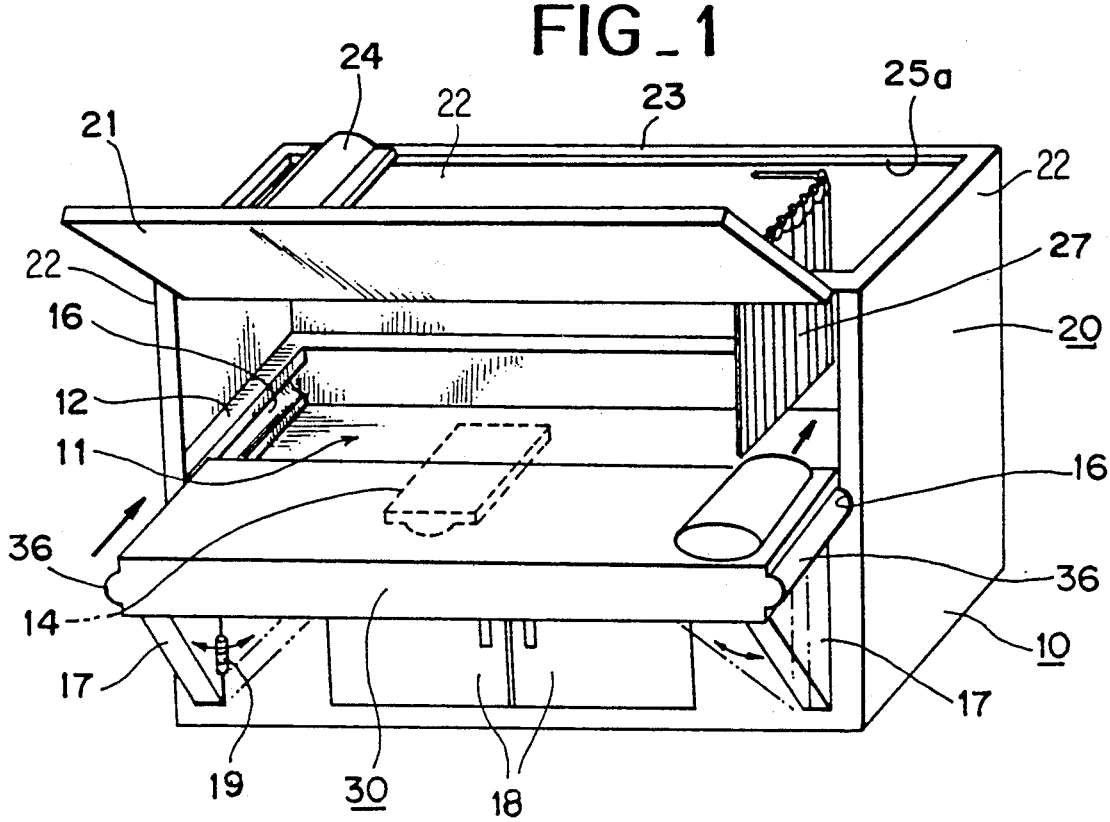
FIG_1
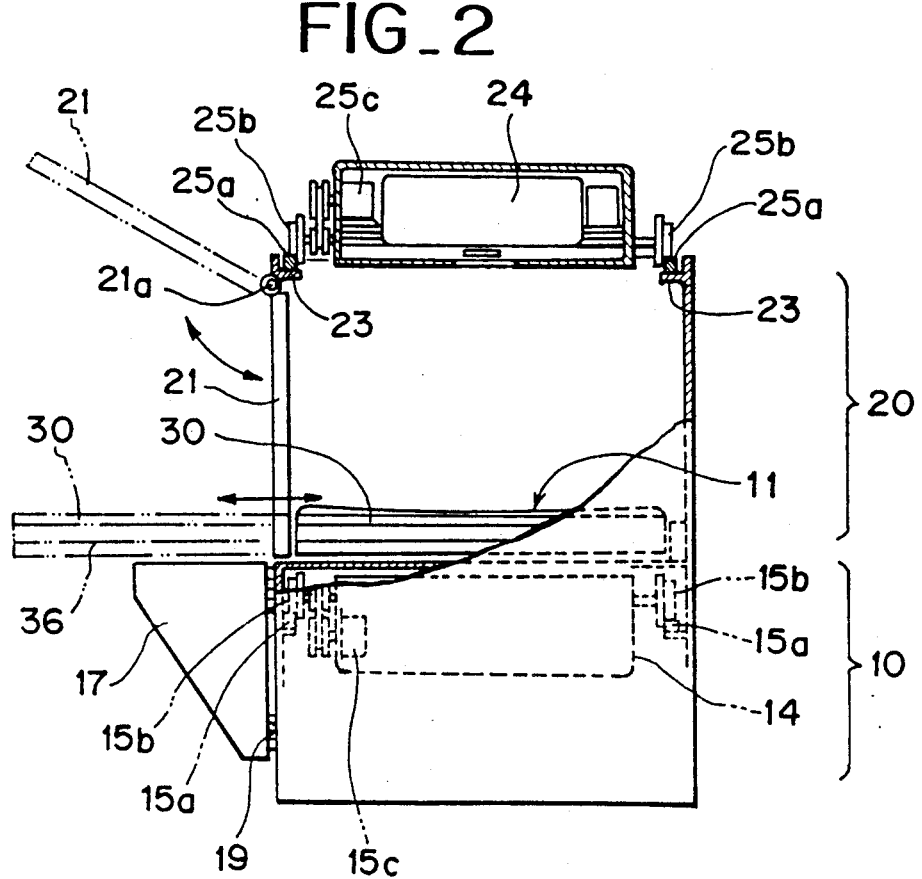
FIG_2

FIG_3
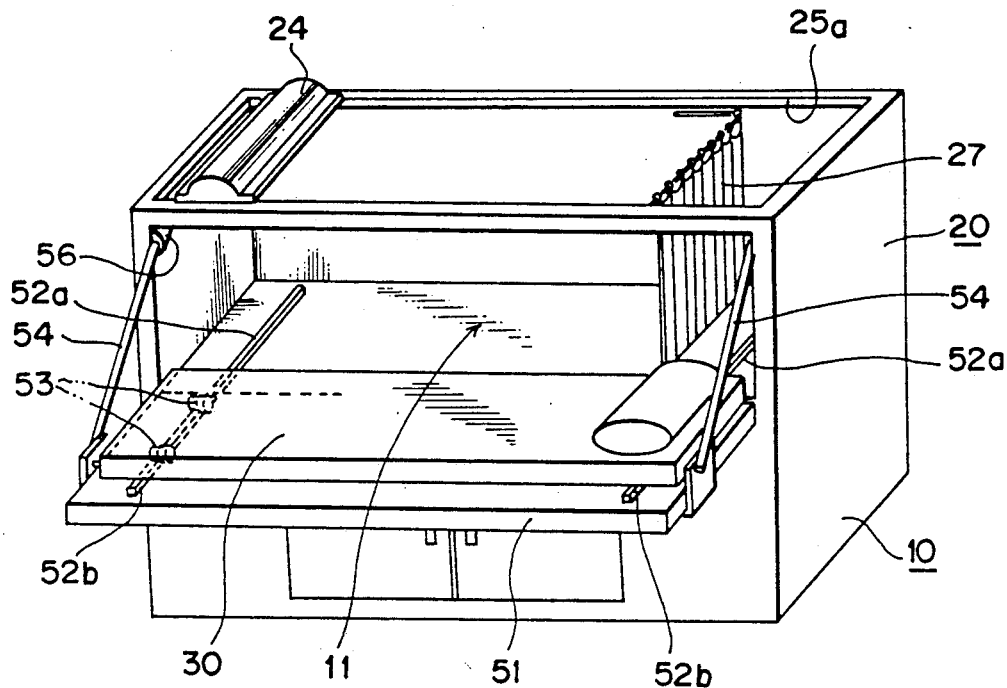
FIG_4
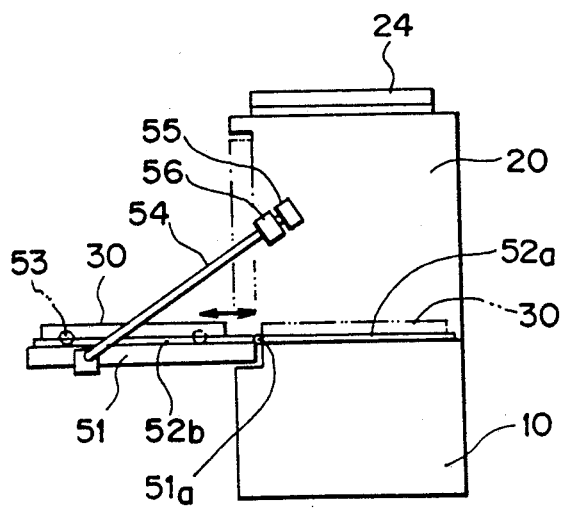
FIG_5
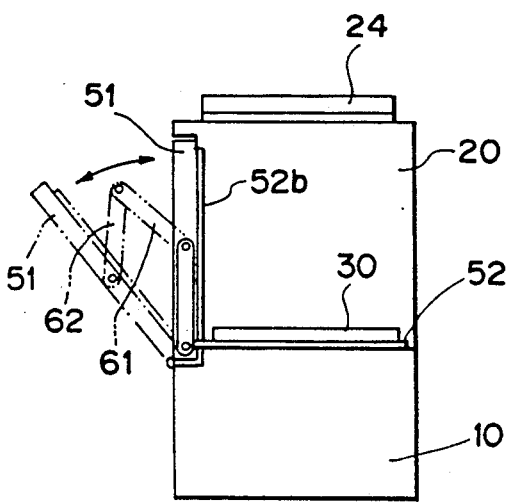

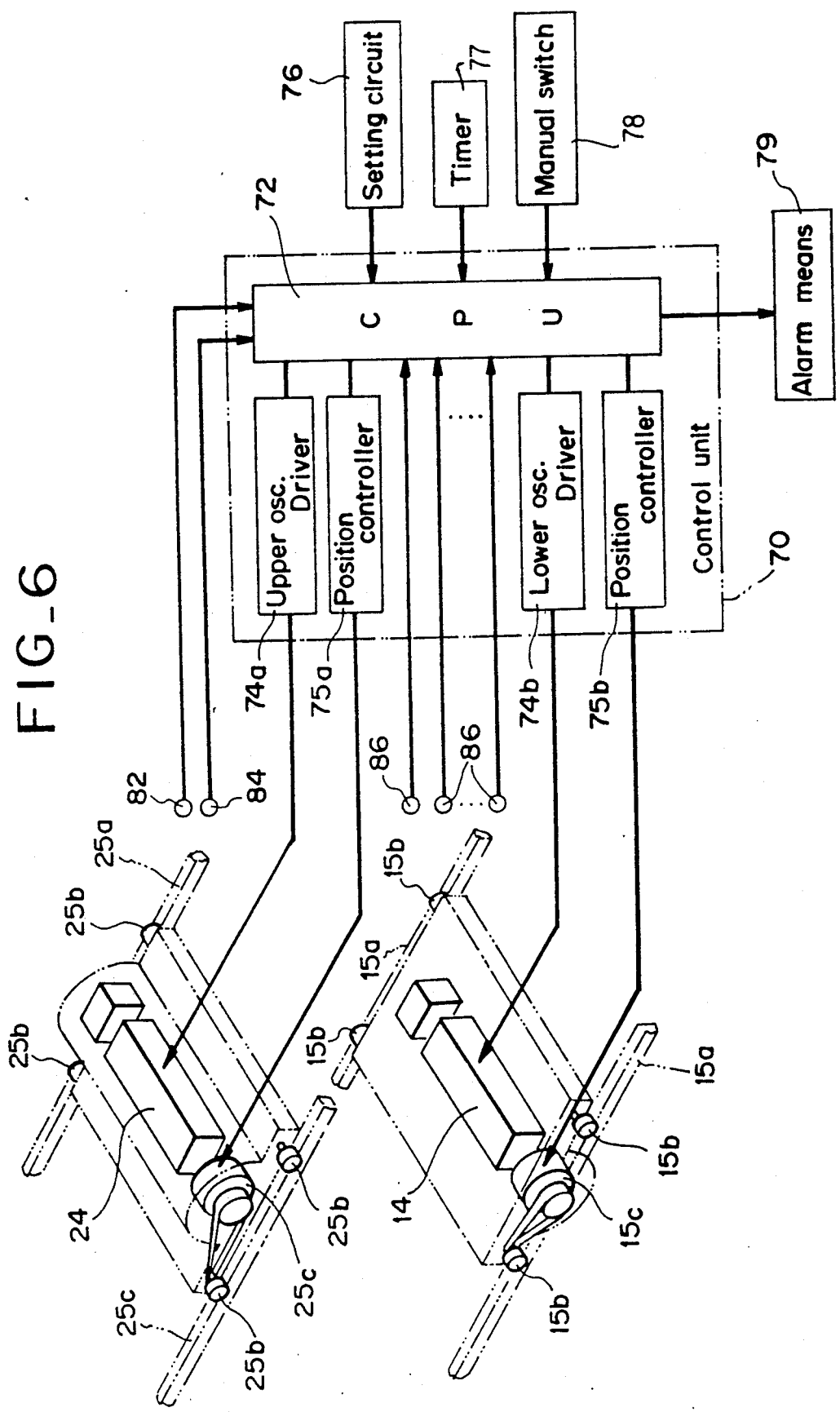
FIG_6

APPARATUS USING MICROWAVES FOR THERMOTHERAPY

BACKGROUND OF THE INVENTION

1. Field of the Invention

This invention relates to a thermotherapeutic apparatus for applying microwaves to a human body for various therapeutic purposes, and more particularly to a medical apparatus using microwaves for thermotherapy which allows a patient to get on and off a treating bed without difficulty in a natural motion posture with the help of a helper or without help and lie down on the treating bed with safety under the treatment.

2. Prior Art

Microwaves having wavelength of less than 6 to 15 meters travel linearly and can be focused on a desired part in a human body. By irradiating the microwaves from the outside of the human body even clothed, the microwaves can heat to the depth of skeletal tissues thereby to subject the human body to thermal treatment. Such thermal treatment using microwaves are being increasingly studied.

The technical system for applications of microwaves having wavelength on the order of 10 cm to a living body for thermal treatment has been established. In the technical system for thermotherapy the irradiation dose and direction of microwaves applied to the living body are predetermined and successively regulated during the treatment so as to accurately control the temperature which rises locally on the outer layer portion or interior of the living body with the microwave irradiation. With such a medical system, thermal treatment having curative effects can be expected. Thus, in recent years the thermotherapy using microwaves have rapidly drawn wide-spread attention for its usefulness in biomedical science.

The inventor of this invention, a pioneer in the use of microwaves for thermotherapy, has successfully developed and proposed a medical apparatus using microwaves for thermotherapy in Japanese Patent Application Public Disclosure No. HEI 1-59146(A) (Corresp. to U.S. patent application Ser. No. 07/198,933). The prior art medical apparatus for thermal treatment comprises a protective frame disposed on a treating bed in a state openable upward on its hinges. However, the protective frame is massive because it is provided with microwave irradiating means and so on. When a patient to be treated is made to lie down on the treating bed, the heavy protective frame must be opened upward. In a case that the patient cannot lie down on the treating bed by himself, the work of placing the patient on the treating bed generally requires two or three helpers, and besides, imposes much labor to the helpers. In a case of the patient with an advanced disease, the patient often complains of bodily pain because the patient is compelled to assume an unnatural posture in lying down on the treating bed.

Furthermore, the conventional medical apparatus noted above is disadvantageous in that the protective frame is necessarily formed of massive frameworks having high strength so as to support the microwave irradiating means, thereby to increase in weight and add to the size.

SUMMARY OF THE INVENTION

In view of the above, an object of the present invention is to provide a medical apparatus using microwaves for thermotherapy, which allows a patient to get on and off a treating bed without difficulty in a natural motion posture suffering no severe pain with the help of a helper or without help and lie down on the treating bed with safety under the treatment.

To attain the object described above, an apparatus using microwaves for thermotherapy according to the present invention comprises a base above which a microwave irradiation region is formed by a protective frame, microwave irradiating means mounted in a horizontally movable state on at least one of the base and protective frame and adapted to irradiate microwaves toward at least a part of the microwave irradiation region, and a treating bed for carrying a patient to be treated, which is disposed on the base slidable in and out of the microwave irradiation region.

On one side of the protective frame, an openable side lid is provided so as to be opened for permitting the treating bed to horizontally slide in and out of the microwave irradiation region inside the protective frame. Though the microwave irradiation region defined within the protective frame is confined, a patient lying on the treating bed which is horizontally movable in and out of the microwave irradiation region can be readily positioned in and out of the microwave irradiation region. With this structure, the patient can be easily made to lie down on the treating bed placed out of and having access to the microwave irradiation region in a natural motion posture with the help of a helper or without help.

BRIEF DESCRIPTION OF THE DRAWINGS

The other objects and features of the present invention will now be explained in detail with reference to the accompanying drawings, wherein:

FIG. 1 is a perspective view schematically showing one embodiment of the medical apparatus using microwaves for thermotherapy according to the present invention;

FIG. 2 is a sectional side view of FIG. 1;

FIG. 3 is a perspective view schematically showing another embodiment of the present invention;

FIG. 4 is a sectional side view of FIG. 3;

FIG. 5 is a perspective view schematically showing still another embodiment of the present invention; and FIG. 6 is an explanatory block circuit diagram showing as one example a control system applicable to the apparatus of the present invention.

DESCRIPTION OF THE PREFERRED EMBODIMENTS

Shown in FIGS. 1 and 2 is one preferred embodiment of the medical apparatus using microwaves for thermal treatment according to the present invention. In the drawings, reference numeral 10 denotes a base with a flat upper surface having a longitudinal length sufficiently longer than the mean stature of adult people; 20 a protective frame fixed on the base 10, within which a microwave irradiation region is defined above the base 10; and 30 a treating bed capable of being slidably moved in and out of the microwave irradiation region defined inside the protective frame 20.

On the base 10 there is formed a bed setting portion 11 for accommodating the treating bed 30 in the aforesaid microwave irradiation region. The bed setting portion 11 is defined by side rib members 12 disposed on the base 10 inside the protective frame 20. Beneath the bed setting portion 11 on the base 10, microwave irradiating means (microwave oscillator) 14 is mounted movably in the longitudinal direction of the base 10. In order to horizontally move the microwave irradiating means 14 in the longitudinal direction of the base 10, the microwave irradiating means 14 is provided on its either side with wheels 15b traveling along rails 15a arranged inside the longitudinal side walls of the base 10 as seen in FIG. 2. The wheels 15b are driven to rotate by means of driving means 15c mounted on the microwave irradiating means 14 so as to give parallel motion to the microwave irradiating means 14. The microwave irradiating means 14 is arranged so as to upwardly irradiate microwaves toward the microwave irradiation region defined inside the protective frame 20.

In the opposite surface portions of the side rib members 12 on the short side walls (right and left side walls in FIG. 2) inside the protective frame 20, there are formed guiding grooves 16.

In this embodiment, a pair of bed supporting members 17 formed of a triangular plate are attached to the front side of the base 10 through hinge means 19 so as to turn about the hinge means 19 as illustrated by the chain line in FIG. 1. Each bed supporting member 17 is rotatably arranged so that the upper side surface of the triangular shaped bed supporting member 17 in the outthrust state thereof becomes flush with the upper surface of the base 10 as indicated by the solid line in FIG. 1.

In this embodiment, since the base 10 is provided on its front side with a double-leafed hinged door 18, the aforesaid bed supporting members 17 are attached one to either side of the hinged door 18 as illustrated. If such a hinged door is not provided, only one bed supporting member may be attached to the center of the front side of the base 10. Thus, the structure and number of the bed supporting member should not be understood as limitative.

The protective frame 20 having four sides is formed with one openable side lid 21 and three stationary side walls 22. The side lid 21 and four side walls 22 are formed of a microwave shielding material which prevents microwaves from passing therethrough. Though in this embodiment the openable side lid 21 is rotatably connected on its upper side to the protective frame 20 through hinge means 21a so as to open upwardly, a double-leafed hinged door capable of opening sidewise may be used in place of the upwardly openable side lid 21.

There is mounted microwave irradiating means (microwave oscillator) 24 in a manner movable along upper frame members 23 formed inside the protective frame 20. The microwave irradiating means 24 is similar in structure to the lower microwave irradiating means 14 disposed inside the base 10 and serves to downwardly irradiate microwaves toward the microwave irradiation region defined by the protective frame 20. In order to horizontally move the microwave irradiating means 24 in the longitudinal direction of the protective frame 20, the microwave irradiating means 24 is provided on its either side with wheels 25b traveling along rails 25a arranged inside the longitudinal side walls of the protective frame 20 as shown in FIG. 2. The wheels 25b are driven to rotate by means of driving means 25c mounted on the microwave irradiating means 24 so as to give parallel motion to the microwave irradiating means 24.

The treating bed 30 is provided on its short side end portions with protruding guide members 36 which are slidably fitted in the guiding grooves 16 formed in the side rib members 12 on the short side walls of the protective frame 10, so that the treating bed 30 for carrying a patient to be treated can be slidably moved in and out of the bed setting portion 11 defined between the side rib members 12.

The protective frame 20 is provided with a flexible shielding screen 27 of a microwave shielding material, by which the patient lying on the treating bed 30 placed in the bed setting portion 11 is partitioned into the patient's head and body.

When subjecting the patient to thermal treatment, the side lid 21 of the protective frame 20 is first opened and the treating bed 30 is drawn out of the bed setting portion 11 defined inside the protective frame 20 upon keeping the bed supporting members 17 in its outthrust state. Therefore, the treating bed 30 thus drawn out is sustained by the bed supporting members 17 in its horizontal state. In this state, since the upper part of the treating bed 30 is open without being obstructed by the protective frame 20, the patient can be made to readily get on the treating bed 30 in a natural motion posture. Then, the treating bed 30 on which the patient lies down is slid into the bed setting portion 11 formed inside the protective frame 20 so as to position the patient lying on the treating bed 30 in the microwave irradiation region defined by the protective frame 20. Thereafter, the upper and lower microwave irradiating means 24, 14 are moved and set in position so that microwaves generated by the microwave irradiating means 24, 14 can be directed toward a specific part of the patient to be treated. Upon completion of thermal treatment, the patient may be released in the reverse manner.

Prior to the thermal treatment to the patient lying on the treating bed 30 placed inside the protective frame 20, the microwave irradiating means 14 and 24 are driven to move in the longitudinal directions of the base 10 and protective frame 20 under control of a control system described later so as to exactly direct the microwaves irradiated from the microwave irradiating means toward the desired part of the patient. The intensity of electric current to be supplied and the time for supplying the electric current for driving the microwave irradiating means 14, 24 placed at their desired positions are regulated in accordance with treating conditions of thermal treatment to be given to the patient.

Though the foregoing embodiment employs the side rib members 12 with the guiding grooves 16 for slidably receiving the protruding guide members 36 formed on the short side portions of the treating bed 30, it is a matter of course that, as a countermeasure, the side rib members 12 may be provided with protruding guide members and the treating bed 30 be correspondingly provided in opposite end portions with guiding grooves for slidably receiving the protruding guide members on the side rib members 12. Furthermore, horizontally moving means for the treating bed may be constituted by rolling contact means such as rollers or balls interposed between the guiding grooves 16 and the protruding guide members 36 to smoothly slide the treating bed 30 in and out of the bed setting portion 11 formed inside the protective frame 20.

Another preferred embodiment will be described with reference to FIGS. 3 and 4.

The medical apparatus in this embodiment has an openable side lid 51 pivotally connected at its lower edge to the base 10 through hinge means 51a so as to open downwardly to its horizontal posture. When the side lid 51 is opened to its horizontal posture as indicated by the solid line in FIG. 4, the upper surface thereof becomes flush with that of the base 10.

The horizontally moving means for the treating bed 30 in this embodiment comprises guide rails 52a, 52b arranged in parallel across the united upper surfaces of the base 10 and the side lid 51, and wheels 53 attached to the lower surface of the treating bed 30 so as to travel along the rails 52a, 52b.

To horizontally hold the side lid 51 in its open state, a pair of hanger rods 54 are used as the bed supporting member. Each hanger rod 54 is pivotally connected at its one end to the side lid 51 and provided on its other end with a stopper 55 for preventing the hanger means 54 from slipping from a holder 56 fixed rotatably on the protector frame 22.

According to this embodiment, the treating bed 30 can easily be drawn out of the bed setting portion 11 defined inside the protective frame 20 only by opening the side lid 51, and therefore, the patient lying on the treating bed 30 can easily be placed in and out of the microwave irradiation region inside the protective frame 20.

In place of the hanger rod 54 noted above, there may be used hanger means comprising foldable links 61, 62 pivotally joined to each other and connected one to the protective frame 20 and other to the treating bed 30 as illustrated in FIG. 5. With the hanger means, the side lid 51 can be retained in its horizontal state.

In FIGS. 4 and 5, like elements are given like reference numerals and therefore will not be described in detail again.

FIG. 6 schematically shows by way of example a driving control system for the medical apparatus described above.

As illustrated, the driving control system of the invention has a control unit 70 comprising upper and lower oscillator driving means 74a, 74b for driving the upper and lower microwave irradiating means 24, 14, position controllers 75a, 75b for rotating the wheels 25a, 15b so as to move the microwave irradiating means 24, 14 respectively to the desired positions, and a processing unit (CPU) 72 for controlling the oscillator driving means 74a, 74b and position controllers 75a, 75b. To the control unit 70, there are connected various input devices such as a setting circuit 76 for activating the microwave irradiating means and so on specifying treating conditions such as the position of the microwave irradiating means and irradiation dose, a timer 77 for setting the time for microwave irradiation, and manual switch means 78 operable by the patient undergoing thermal treatment on the treating bed or a helper therefor can manually control the microwave irradiating means and so on. Further connected to the control unit 70 is alarm means 79 which issues warnings when the manual switch means 78 is manually operated or abnormality is brought about.

In addition, to the control unit 70 there are connected a limit switch 82 which assumes its on state when the side lid 21 (or 51) is completely closed and a limit switch 84 which assumes its on state when the bed 30 is closely fitted in position into the bed setting portion 11 defined inside the protective frame 20. Therefore, if one of the limit switches 82, 84 does not turn on, the medical apparatus is inactivated.

The control unit 70 is connected to thermal sensors 86 which are attached to a plurality of parts on the patient's body to take a safety measure. By means of the thermal sensors 86, temperature data are successively obtained from the patient's body and fed to the control unit 70 so that heating temperature on the patient's body can be adequately regulated on the basis of temperature values predetermined according to various symptoms. Moreover, when the heating temperature on the patient's body is elevated abnormally, the microwave irradiating means are suspended and a warning is issued from the alarm means 79.

Thus, the control system noted above allows the position and time of microwave irradiation to be freely determined with ease and can maintain the safety during thermal treatment. It goes without saying that the control system is not limited only to the disclosed structure shown in FIG. 6 and may instead be of any electrical structures and provided with further functions as occasion arises.

As is clear from the foregoing, in accordance with the present invention it is possible to provide the medical apparatus using microwaves for thermal treatment, capable of making a patient to get on and off a treating bed without difficulty in a natural motion posture suffering no severe pain with the help of a helper or without help and lie down on the treating bed with safety under the treatment. Besides, since the medical apparatus is provided with the control system including various safety switch means and thermal sensors, the safety under the thermal treatment can be maintained and the medical apparatus can be handled easily and simply.

Although the present invention has been described in its preferred forms with a certain degree of particularity, it is understood that the present disclosure of the preferred forms can be modified in the details of construction and the combination and arrangement of elements may be resorted to without departing from the spirit and the scope of the invention as hereinafter claimed.

What is claimed is:

1. An apparatus using microwaves for thermotherapy which comprises a base having a flat upper surface, a protective frame fixed on said base and defining inside a microwave irradiation region above said base, microwave irradiation means mounted in a horizontally movable state on at least one of said base and protective frame and adapted to irradiate microwaves toward at least a part of said microwave irradiation region, a treating bed for allowing a patient to lie down thereon, which is disposed movably on said base so as to slide in and out of said microwave irradiation region, and horizontally moving means interposed between said treating bed and base for horizontally moving said treating bed relative to said base.

2. An apparatus according to claim 1 wherein said treating bed has protruding guide members on its either side, and said protective frame is provided inside with opposite grooves which receive said protruding guide members on said treating bed.

3. An apparatus according to claim 1 further comprising an openable side lid disposed on one side of said protective frame so as to allow said treating bed to be slid in and out of said microwave irradiation region when said side lid is open.

4. An apparatus according to claim 3 further comprising hinge means for rotatably connecting said openable side lid to said base so as to permit said lid to open downwardly, guide rails arranged in parallel across the upper surface of said base and said side lid when said lid opens, and wheels attached to said treating bed in a movable fashion along said rails.

5. An apparatus according to claim 3 further comprising at lest one bed supporting member for horizontally supporting said treating bed drawn out of the microwave irradiation region, said bed supporting member being formed of a triangular shaped plate and rotatably attached to said base.

6. An apparatus according to claim 3 further comprising at least one bed supporting member for horizontally supporting said treating bed drawn out of the microwave irradiation region, said bed supporting member being formed of a hanger rod connected between said side lid and said protective frame and a holder rotatably supporting said hanger rod on said protective frame.

7. An apparatus according to claim 1 wherein said protective frame is provided inside with a flexible shielding screen of a microwave shielding material.

8. An apparatus according to claim 1 wherein said microwave irradiating means are movably mounted in said protective frame and said base.

* * * * *